US012799208B2

(12) United States Patent
Liu

(10) Patent No.: US 12,799,208 B2
(45) Date of Patent: Nov. 17, 2026

(54) ANTI-CD276 mAb TO TARGET BREAST CANCER

(71) Applicant: THE UAB RESEARCH FOUNDATION, Birmingham, AL (US)

(72) Inventor: Xiaoguang Liu, Vestavia Hills, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 464 days.

(21) Appl. No.: 18/434,087

(22) Filed: Feb. 6, 2024

(65) Prior Publication Data

US 2024/0279337 A1 Aug. 22, 2024

Related U.S. Application Data

(60) Provisional application No. 63/484,794, filed on Feb. 14, 2023.

(51) Int. Cl.

| | |
|---|---|
| ***C07K 16/28*** | (2006.01) |
| ***A61K 39/00*** | (2006.01) |
| ***A61K 47/68*** | (2017.01) |
| ***A61P 35/00*** | (2006.01) |

(52) U.S. Cl.
CPC ...... *C07K 16/2827* (2013.01); *A61K 47/6881* (2017.08); *A61P 35/00* (2018.01); *C07K 16/2863* (2013.01); *A61K 2039/505* (2013.01); *C07K 2317/565* (2013.01); *C07K 2317/622* (2013.01)

(58) Field of Classification Search
CPC ........... C07K 16/2827; C07K 16/2863; C07K 2317/565; C07K 2317/622; A61K 47/6881; A61K 2039/505; A61P 35/00
See application file for complete search history.

(56) References Cited

U.S. PATENT DOCUMENTS

2020/0338209 A1* 10/2020 Benatuil .............. A61K 31/337

* cited by examiner

*Primary Examiner* — Samira J Jean-Louis
*Assistant Examiner* — Peter Johansen
(74) *Attorney, Agent, or Firm* — THOMAS | HORSTEMEYER, LLP

(57) ABSTRACT

Disclosed herein is anti-human CD276 mAb expressing the Fc-fused fragments from the extracellular domain of human CD276 (Leu29-Pro245), producing the N-glycosylated peptides as immunogen, and generating hybridoma cells through fusing mouse splenocytes and myeloma cells. The specific targeting of cancer cells and intracellular release of potent drugs enables high anti-cancer efficiency and minimal side effects.

12 Claims, 14 Drawing Sheets

Specification includes a Sequence Listing.

ANTI-CD276 mAb TO TARGET BREAST CANCER

CROSS-REFERENCE TO RELATED APPLICATIONS

This application claims benefit of U.S. Provisional Application No. 63/484,794, filed Feb. 14, 2023, which is hereby incorporated herein by reference in its entirety.

SEQUENCE LISTING

This application contains a sequence listing filed in ST.26 format entitled "222119-1210 Sequence Listing" created on Feb. 6, 2024, and having 10,322 bytes. The content of the sequence listing is incorporated herein in its entirety.

BACKGROUND OF THE INVENTION

Triple-negative breast cancers accounting for 15-20% of breast cancers are highly aggressive, metastatic in lung, bone and brain, and heterogenous. CD276 (B7-H3), which inhibits NK and T cell functions via antigen-presenting cells and is associated with angiogenesis, invasion, metastasis and poor prognosis in cancer patients, was detected in >80% of breast cancer tissues (Sun J, et al. Onco Targets Ther. 2014 7:1979-86; Bachawal S V, et al. Cancer Res. 2015 75(12): 2501-9; Liu C, et al. Mol Med Rep. 2013 7(1):134-8).

SUMMARY OF THE INVENTION

As disclosed herein, there is high expression of CD276 in multiple TNBC cell lines and in 60% of primary TNBC samples. Therefore, disclosed herein is anti-human CD276 mAb expressing the Fc-fused fragments from the extracellular domain of human CD276 (Leu29-Pro245), producing the N-glycosylated peptides as immunogen, and generating hybridoma cells through fusing mouse splenocytes and myeloma cells. The unique aspects of this anti-CD276 mAb include: 1) specifically targeting the N-glycosylated extracellular domain of CD276 surface receptor, 2) activating NK/T immune cells and the effector immune function, 3) delivering chemotherapy via antibody-drug conjugate or other targeting delivery vehicle.

Low clinical efficiency and high drug resistance pose a major challenge in current TNBC treatment. The proposed antibody-drug conjugate (ADC) have integrated anti-cancer mechanisms: direct TNBC cell death caused by potent drug (microtubulin polymerization) and induction of anti-CD276 immune response.

The details of one or more embodiments of the invention are set forth in the accompanying drawings and the description below. Other features, objects, and advantages of the invention will be apparent from the description and drawings, and from the claims.

BRIEF DESCRIPTION OF FIGURES

FIG. 1B shows Representative images of low, medium and high CD276 expression.

FIGS. 2A to 2C: Anti-CD276 mAb development, production and evaluation. FIG. 3A shows Rank of anti-CD276 mAb producing hybridoma clones using ELISA titration (data represent mean±SEM, n=3). The top clone with the highest CD276 productivity was selected and used in this study. FIG. 2B shows The cell growth of anti-CD276 mAb producing hybridoma in shaker flask (data represent mean±SEM, n=3). Viable cell density (VCD): ▲, cell viability: Δ. FIG. 2C shows Analysis of TNBC cells (MDA-MB-231, MDA-MB-468, and 4T1) surface binding by anti-CD276 using flow cytometry. Staining conditions: 1 μg of CD276 mAb-AF647, $1\times10^6$ TNBC cells, room temperature, and 30 minutes.

FIG. 4A shows IVIS imaging to confirm TNBC-specific targeting of anti-CD276 mAb-Cy5.5 in 4T1-FLuc xenografted BALB/cJ models. FIG. 4B shows IVIS imaging to confirm TNBC-specific targeting of CD276 mAb-Cy5.5 in MDA-MB-468-FLuc xenografted NSG models. The live-animal images were collected at 24 hr post tail vein injection of fluorescent dye Cy5.5-labelled mAb, followed with scarification, tumor and organs harvest and ex vivo imaging.

FIG. 5A shows ADC synthesis efficiency and DAR analysis using HPLC equipped with a MAbPac HIC-Butyl column. FIG. 5B shows Cytotoxicity analysis of the CD276 ADC in TNBC MDA-MB-231 cells (▲), MDA-MB-468 cells (■) and 4T1 cells (●).

FIG. 6 shows The normalized body weight after treatment. FIG. 6B shows Tumor volume changes post treatment. Treatment was started on Day 7 following schedule of Q4Dx4 as indicated by the black arrow. Tumor volume was measured with calipers, and calculated as ellipsoid. Data were presented as mean±SEM, n=7. PBS (■), 8 mg/kg of anti-CD276 mAb (♦), 8 mg/kg of ADC (■), and 20 mg/kg of ADC (▲). FIG. 6C shows Wet weight of harvested tumors. *P<0.005 vs. PBS using ANOVA followed by Dunnett's t-test.

FIG. 7A shows Representative images of IHC staining of the $CD276^+$ PDX xenograft tissues. Scale bar equals to 20 μm. FIG. 7B shows Tumor volume post treatment (n=7). PBS (♦) and 8 mg/kg of ADC (●). Arrow indicating the i.v. injection of control or therapy. FIG. 7C shows Wet weight of harvested tumors. FIG. 7D shows The normalized body weight during the whole animal study. *P<0.005 vs. PBS using ANOVA followed by Dunnett's t-test.

DETAILED DESCRIPTION

Figure 1A:
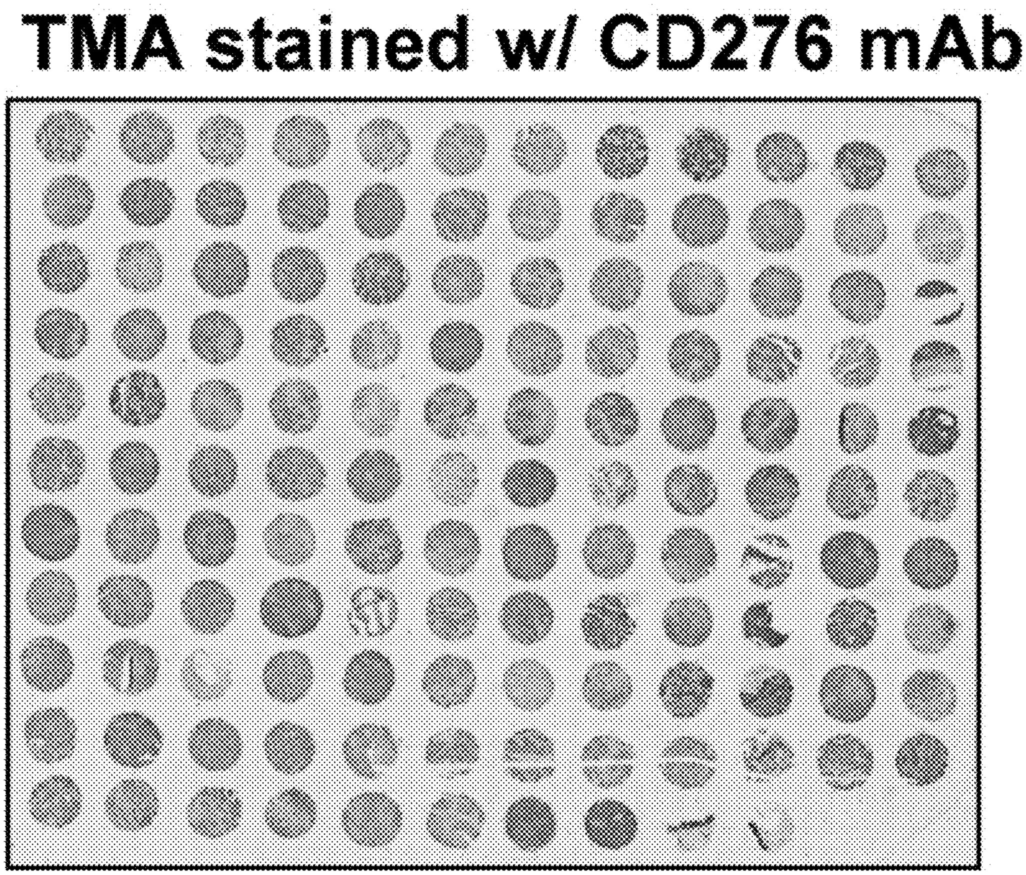
FIGS. 1A and 1B: Evaluation of CD276 surface receptor in TNBC patient tissue microarray (TMA).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Triple-negative breast cancers (TNBCs) accounting for 15-20% of breast cancers are highly aggressive, metastatic in lung, bone and brain, and heterogenous. Standard cytotoxic chemotherapies (e.g. anthracycline-taxane) (Liedtke, C. et al. J Clin Oncol 26:1275-1281 (2008); Silver, D. P. et al. J Clin Oncol 28:1145-1153 (2010); Nedeljkovic, M. & Damjanovic, A. Cells 8 (2019); Wein, L. & Loi, S. Breast 34 Suppl 1:S27-S30 (2017)) are the main treatment strategy for TNBCs. The drug resistance, high recurrence rate (>50%) post primary treatment (Silver, D. P. et al. J Clin Oncol 28:1145-1153 (2010); Nedeljkovic, M. & Damjanovic, A. Cells 8 (2019); Wein, L. & Loi, S. Breast 34 Suppl 1:S27-S30 (2017); Martinelli, E., et al. Clin Exp Immunol 158:1-9 (2009)) and adverse effects minimize the clinical benefits of these drugs (Al-Mahmood, S., et al. Drug Deliv Transl Res 8:1483-1507 (2018); Lebert, J. M., et al. Curr Oncol 25:S142-S150 (2018)). Monoclonal antibodies (mAbs) that target epidermal growth factor receptor (EGFR) (Martinelli, E., et al. Clin Exp Immunol 158:1-9 (2009); Flynn, J. F., et al. J Oncol 2009:526963 (2009)) and folate receptor (Cheung, A. et al. Clin Cancer Res 24:5098-5111 (2018); Frontera, E. D. et al. Breast Cancer Res Treat 172:551-560 (2018)) showed limited efficacy as a single agent in clinical trials. FDA approved an immunotherapy-chemotherapy, Atezolizumab and Abraxane, to treat PD-L1$^{+}$ TNBC (Romero, D. Nat Rev Clin Oncol 16:6 (2019); Marra, A., et al. BMC Med 17:90 (2019); Zhu, X. et al. Cancer Biol Ther 20:1105-1112 (2019)), indicating the great potential of combined therapies. Antibody-drug conjugates (ADCs) have been developed to treat various cancers (de Claro, R. A. et al. Clin Cancer Res 18:5845-5849 (2012); Doi, T. et al. Lancet Oncol 18:1512-1522 (2017)), which combine the advantages of mAbs, such as cancer-targeting, antibody-dependent cell-mediated cytotoxicity (ADCC) and other immune responses, and highly potent payload (Zhou, L., et al. Cancer Lett 352:145-151 (2014); Almasbak, H., et al. J Immunol Res 2016:5474602 (2016); Dai, H., et al. J Natl Cancer Inst 108 (2016); Magee, M. S. & Snook, A. E. Discov Med 18:265-271 (2014); Zhang, B. L. et al. Sci China Life Sci 59:340-348 (2016); Kunert, R. & Reinhart, D. Appl Microbiol Biotechnol 100:3451-3461 (2016); Polakis, P. Pharmacol Rev 68:3-19 (2016)). Despite the promising clinical efficiency of ADC, no targeted ADC is available to eliminate TNBC.

Disclosed herein is an isolated anti-human CD276 monoclonal antibody that selectively binds the extracellular domain of CD276 (Leu29-Pro245). Therefore, recombinant antibodies and other proteins comprising the antigen binding regions from these antibodies are also disclosed. Also disclosed are recombinant, humanized, and/or chimeric antibodies comprising at least the antigen binding regions of one or more of these antibodies.

In some embodiments, the anti-CD276 antibody can comprise a variable heavy ($V_H$) domain having CDR1, CDR2 and CDR3 sequences and a variable light ($V_L$) domain having CDR1, CDR2 and CDR3 sequences.

For example, in some embodiments, the CDR1 sequence of the $V_H$ domain comprises the amino acid sequence GYTFTEYT (SEQ ID NO:1), CDR2 sequence of the $V_H$ domain comprises the amino acid sequence NNPNTGGT (SEQ ID NO:2), CDR3 sequence of the $V_H$ domain comprises the amino acid sequence SRSGNDVGWYFAV (SEQ ID NO:3), CDR1 sequence of the $V_L$ comprises the amino acid sequence SSVSY (SEQ ID NO:4), CDR2 sequence of the $V_L$ domain comprises the amino acid sequence DTS, and CDR3 sequence of the $V_L$ domain comprises the amino acid sequence QQWSSNPLT (SEQ ID NO:5).

Therefore, in some embodiments, the $V_H$ domain comprises the amino acid sequence

```
                                          (SEQ ID NO: 6)
EVQLQQSGPELVKPGASVKISCKTSGYTFTEYTMHWVKQSHGKSLEWIGS

NNPNTGGTTYNQKFKDKATLTVDKSSNTAYMELRSLTSDDSAVYYCSRSG

NDVGWYFAVWGAGTTVTVSS.
```

Therefore, in some embodiments, the $V_L$ domain comprises the amino acid sequence

```
                                          (SEQ ID NO: 7)
QIVLTQSPAIMSASPGEKVTMTCTATSSVSYMHWYQQKSDSSPKRWIYDT

SKLASGVPDRFSGSGSGTSYSLIISSMEAEDAATYYCQQWSSNPLTFGAG

TKLELKR.
```

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bis-pecific antibodies, which are obtained by the noncovalent association of two single-chain fusion products, consisting of the VH domain from one antibody connected by a short linker to the VL domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein. Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest (e.g., CD276). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In some embodiments, the anti-CD276 binding agent is single chain variable fragment (scFv) antibody. The affinity/specificity of an anti-CD276 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3). The heavy and light chains are preferably separated by a linker. Suitable linkers for scFv antibodies are known in the art. In some embodiments, the linker comprises the amino acid sequence GGGGSGGGGSGGGGS (SEQ ID NO:8).

In some embodiments, the anti-CD276 antibody is a recombinant full-length antibody. For example, in some embodiments, the heavy chain full length sequence is: MGWSWIFLFLLSGTAGVLSEVQLQQSGPELVKP-GASVKISCKTSGYTFTEYTMHWVKQSHGK SLEWIG-SNNPNTGGTTYNQKFKDKATLTVDKSSN-TAYMELRSLTSDDSAVYYCSRSGNDVGW YFAVWGAGTTVTVSSAKTTAPSVY-PLAPVCGDTTGSSVTLGCLVKGYF-PEPVTLTWNSGSLSS GVHTFPAVLQSD-LYTLSSSVTVTSSTWPSQSITCNVAHPASSTKVDK-KIEPRGPTIKPCPPCKC PAPNLLGGPSVFIFPP-KIKDVLMISLSPIVTCVVVDVSEDDPDVQISWFVNN-VEVHTAQTQTHRE DYN-STIRVVSTLPIQHQDWMSGKEFKCKVNNKDLPSPIER-TISKIKGLVRAPQVYILPPPAEQLS RKDVSLTCLVVGFNPGDISVEWTSNGHTEENYKD-TAPVLDSDGSYFIYSKLNMKTSKWEKTDS FSCNVRHEGLKNYYLKKTISRTPGK (SEQ ID NO:9). For example, in some embodiments, the light chain full length sequence is:

```
                                          (SEQ ID NO: 10)
MDYQVQIFSFLLISASVIISRGQIVLTQSPAIMSASPGEKVTMTCTATSS

VSYMHWYQQKSDSSPKRWIYDTSKLASGVPDRFSGSGSGTSYSLIISSME

AEDAATYYCQQWSSNPLTFGAGTKLELKRADAAPTVSIFPPSSEQLTSGG

ASVVCFLNNFYPKDINVKWKIDGSERQNGVLNSWTDQDSKDSTYSMSSTL

TLTKDEYERHNSYTCEATHKTSTSPIVKSFNRNEC.
```

EXAMPLES

Example 1: CD276-Targeted Antibody-Drug Conjugate to Treat Triple-Negative Breast Cancer

INTRODUCTION

Recently, the cell surface expression of glycoprotein CD276 (B7-H3), which is comprised of two Ig-like V-type and two Ig-like C2-type extracellular domains and seven N-linked glycosylation sites (Chen R, et al. J Proteome Res. 2009 8(2):651-61), was detected in more than 80% of breast cancer tissues (Sun J, et al. Onco Targets Ther. 2014 7:1979-86; Bachawal S V, et al. Cancer Res. 2015 75(12): 2501-9; Liu C, et al. Mol Med Rep. 2013 7(1):134-8). This study demonstrated high expression of CD276 in multiple TNBC cell lines and majority of primary TNBC samples.

The CD276 is also associated with angiogenesis, invasion, metastasis and poor prognosis in cancer patients (Sun J, et al. Onco Targets Ther. 2014 7:1979-86; Ye Z, et al. Cell Physiol Biochem. 2016 39(4):1568-80; Castellanos J R, et al. Am J Clin Exp Immunol. 2017 6(4):66-75; Kraan J, et al. Br J Cancer. 2014 111(1):149-56; Picarda E, et al. Clin Cancer Res. 2016 22(14):3425-31). Importantly, literature (Bachawal S V, et al. Cancer Res. 2015 75(12):2501-9; Seaman S, et al. Cancer Cell. 2017 31(4):501-15 e8) showed that CD276 is nearly undetectable or low in important normal organs (brain, heart, lung, liver, pancreas, kidney, and others) and normal breast tissue, making it an appealing target for cancer treatment. Of note, CD276 expression is limited at steady state in normal fibroblasts and endothelial cells (ECs) but is highly detectable in tumor-associated ECs (Picarda E, et al. Clin Cancer Res. 2016 22(14):3425-31; Seaman S, et al. Cancer Cell. 2017 31(4):501-15 e8; Seaman S, et al. Cancer Cell. 2007 11(6):539-54). CD276 is also involved in the inhibition of natural killer (NK) and T cells (Pardoll D M. Nat Rev Cancer. 2012 12(4):252-64; Vigdorovich V, et al. Structure. 2013 21(5):707-17; Chen C, et al. Exp Cell Res. 2013 319(1):96-102) and the production of effector cytokine (e.g., IFN-γ, TNF-α) (Suh W K, et al. Nat Immunol. 2003 4(9):899-906; Prasad D V, et al. J Immunol. 2004 173(4):2500-6). It is found that the blockade of CD276 in antigen-presenting cells (APC) could neutralize the inhibitory signaling in NK/T immune cells and enable the effector immune function (Picarda E, et al. Clin Cancer Res. 2016 22(14):3425-31; Maeda N, et al. Ann Surg Oncol. 2014 21 Suppl 4:S546-54). The anti-CD276 enoblituzumab (Picarda E, et al. Clin Cancer Res. 2016 22(14):3425-31) and bispecific antibody targeting CD276/CD3 (MGD009) (Weidle U H, et al. Semin Oncol. 2014 41(5):653-60) are being developed and evaluated to treat melanoma, colorectal, prostate and lung cancers in Phase I clinical trial (Picarda E, et al. Clin Cancer Res. 2016 22(14):3425-31). All these previous studies indicated that CD276 is a promising and safe target for TNBC patients.

The US FDA has approved a combined Atezolizumab (immune checkpoint inhibitor) and Abraxane (nab-paclitaxel) to treat PD-L1$^+$ TNBC (Romero D. Nat Rev Clin Oncol. 2019 16(1):6; Marra A, et al. BMC Med. 2019 17(1):90; Zhu X, et al. Cancer Biol Ther. 2019 20(8):1105-12) and an antibody-drug conjugate (ADC), i.e. Sacituzumab Govitecan, to treat trophoblast cell-surface antigen 2 (Trop-2)$^+$ TNBC (Bardia A, et al. N Engl J Med. 2021 384(16):1529-41; Bardia A, et al. N Engl J Med. 2019 380(8):741-51; McGuinness J E, et al. Expert Opin Biol Ther. 2020:1-11; Seligson J M, et al. Ann Pharmacother. 2021 55(7):921-31; Wahby S, et al. Clin Cancer Res. 2021 27(7):1850-4). These achievements demonstrated the great potential of targeted therapies and the combination of cancer-targeting antibody with highly potent chemotherapy to treat TNBC pateints. Therefore, this study developed and evaluated a new mAb that targets the glycosylated extracellular domain of CD276 surface receptor and a CD276-targeting ADC.

The objective of this study was to evaluate CD276 as a surface receptor of TNBC, develop a new mAb that targets the glycosylated extracellular domain, construct ADC, and evaluate the anti-cancer cytotoxicity in three TNBC cell lines and the anti-tumor efficacy using both cell line-derived xenograft models and PDX models.

Materials and Methods

Cell Lines and Culture Media

The human TNBC cell lines, including MDA-MB-231 (ATCC, Manassas, VA, USA), MDA-MB-468 (ATCC), MDA-MB-231-FLuc (GenTarget, San Diego, CA, USA), and MDA-MB-468-FLuc (GeneCopoeia, Rockville, MD, USA), were maintained in DMEM medium supplemented with 10% fetal bovine serum (FBS, v/v) and 1% Pen/Strep (v/v). The mouse TNBC cell lines 4T1 and 4T1-FLuc (ATCC) were cultivated in RPMI-1640 medium supplemented with 10% FBS and 1% P/S. The anti-CD276 mAb hybridoma cells were cultivated in DMEM with the addition of 4.5 g/L glucose, 6 mM L-glutamine, 1 mM sodium pyruvate, 10% FBS and 1% P/S. All cell lines were incubated at 37° C. and 5% $CO_2$ in a humidified incubator (Caron, Marietta, OH, USA). All media, supplements and bioreagents used in this study were purchased from Fisher Scientific (Waltham, MA, USA) unless otherwise specified.

The TNBC ($ER^-/PR^-/HER2^-$) patient tissue microarray (TMA) was purchased from US Biomax (Derwood, MD, USA) to detect CD276 expression with immunohistochemistry (IHC) staining (Si Y, et al. Cancer Gene Therapy. Cancer Gene Therapy. 2020; Si Y, et al. Vaccines (Basel) 2021 Aug. 10; 9(8):882; Guenter R, et al. Surgery. 2021 170(1):351; Guenter R, et al. Surgery. 2020 167(1):189-96). First, the TMA slide was baked overnight at 60° C., deparaffinized with xylene, and hydrated in ethanol and deionized water. Then the sectioned tissues were subjected to antigen retrieval in 0.01 M sodium citrate buffer (pH 6) for 5 mins, washed gently in deionized water, and transferred to solution comprised of 0.05 M Tris, 0.15 M NaCl and 0.1% Triton-X-100 (TBST, pH 7.6). The endogenous peroxidase was blocked with 3% $H_2O_2$ for 15 mins and slides were incubated with 5% normal goat serum for 45 mins to reduce nonspecific background staining. All slides were incubated at 4° C. overnight with anti-CD276 antibody (Abcam, Rabbit monoclonal, 1/500 dilution). After washing with TBST, slide was incubated with goat anti-rabbit secondary antibody conjugated with HRP (Abcam ab6721, 1:1000). Finally, the stained TMA slide was scanned with Lionheart FX Automated Microscope (BioTek, Winooski, VT, USA) and images were processed with Gen5 software. Following previously established method (Si Y, et al. Cancer Gene Ther. 2020), ImageJ was used to score the CD276 expression in the stained TMA. Briefly, the expression score of CD276 was calculated as $(red_{intensity}-blue_{intensity})/blue_{intensity}\times100$ with definition of high expression with score of >10, medium expression with score of 6-10, low expression with score of 3-6, and no or minimal expression with score of 0-3.

Anti-CD276 (87-H3) mAb Development and Production

The N-glycosylated peptide cloned from the extracellular domain (Leu29-Pro245) of human CD276 was used to stimulate immune response in BALB/cJ mice (The Jackson Laboratory, Bar Harbor, ME, USA). As described previously (Si Y, et al. Cancer Gene Therapy. Cancer Gene Therapy. 2020; Si Y, et al. Vaccines (Basel) 2021 Aug. 10; 9(8):882), blood samples were collected from tail vein to titrate serum concentration of CD276 mAb using ELISA at 14-21 days post-immunization. Once mAb was detected, splenocytes were harvested and fused with myeloma cells Sp2/0-Ag14 (ATCC) to generate hybridoma, followed with limiting dilution with seeding density of 1~4 cells/well in 96-well plates. The top hybridoma clone was identified based on the anti-CD276 mAb titer and used to produce mAb in this study. The adherent hybridoma cells were adapted to suspension culture in serum-free medium and fed-batch culture was performed in shaker flask and/or spinner flask for mAb production which was fed with 3.5 g/L of Cell Boost, 2-4 g/L of glucose and 2-4 mM of L-glutamine (Yang S, et al. Journal of Biopharmaceuticals Bioprocessing. 2013 1(2): 133-6; Xu N, et al. Biochem Eng J. 2017 124:122-9). Liquid chromatography system (Bio-Rad, Hercules, CA, USA), which is equipped with Bio-Scale Mini UNOsphere SUPrA affinity chromatography cartridges (Protein A column, Bio-Rad), was utilized for mAb purification following an established procedure (Si Y, et al. Cancer Gene Therapy. Cancer Gene Therapy. 2020; Si Y, et al. Vaccines (Basel) 2021 Aug. 10; 9(8):882; Xu N, et al. Biochem Eng J. 2017 124:122-9; Ou J, et al. PLOS ONE. 2018; Xu N, et al. Biochemical Engineering Journal. 2018; Chen K, et al. Pharmaceuticals (Basel). 2021 14(5); Xu N, et al. Frontiers of Chemical Science & Engineering. 2017 9(3):376-80). The mobile phase A of 0.02 M sodium phosphate and 0.02 M sodium citrate (pH 7.5) and phase B (elution buffer) of 0.1 M sodium chloride and 0.02 M sodium citrate (pH 3.0) were used.

Anti-CD276 mAb-DM1 Conjugation and Characterization

The ADC was constructed following a previously reported platform with process optimization. Specifically, the purified anti-CD276 mAb was buffer exchanged to phosphate buffered saline (PBS) and concentrated to 2.5 mg/mL using 10 kDa MWCO PES concentrators. The 2.5 mg/mL of mAb, 10 mg/mL of Sulfo-SMCC linker, and 10 mM of Mertansine (DM1) were mixed with a molar ratio of 1:14:18.2 in PBS with a final reaction volume of 400 μL. The conjugation was performed at 37° C. for 2 hrs, and the synthesized ADC was purified using Protein A column with liquid chromatography system. The ADC purity and drug-antibody ratio (DAR) were tested using HPLC (Shimadzu, Columbia, MD, USA) equipped with a MAbPac hydrophobicity interaction chromatography (HIC)-butyl column (5 μm, 4.6×100 mm). The mobile phase A of 2 M ammonium sulfate and 100 mM sodium phosphate at pH 7.0 and mobile phase B of 100 mM sodium phosphate at pH 7.0 were used in HPLC analysis.

Flow Cytometry Analysis

The surface binding rates of the anti-CD276 mAb in TNBC cell lines, including MDA-MB-231, MDA-MB-468 and 4T1, were tested by flow cytometry analysis following reported protocols (Si Y, et al. Cancer Gene Therapy. Cancer Gene Therapy. 2020; Si Y, et al. Vaccines (Basel) 2021 Aug. 10; 9(8):882; Ou J, et al. PLOS ONE. 2018; Chen K, et al. Pharmaceuticals (Basel). 2021 14(5); Si Y, et al. Pharmaceutics. 2020 12(11):1079-90; Si Y, et al. Biotechnol J. 2019:e1900163; Si Y, et al. Eng Life Sci. 2021 21(1-2):37-44; Si Y, et al. Cancers (Basel). 2021 13(15); Ou J, et al. J Biol Eng. 2019 13:34). The anti-CD276 mAb was labeled with fluorescent Alexa Fluor™ 647 labelling kit (Life Technologies, part of Fisher). One million TNBC cells were stained with 5 μg of anti-CD276 mAb-AF647 at 37° C. for 30 mins. After washing three times with PBS, the stained cells were analyzed using BD LSRII flow cytometer (BD Biosciences, San Jose, CA, USA) with Flow-Jo software for data processing.

Live-Cell Confocal Microscopy

The surface binding and internalization of CD276 mAb was evaluated with live-cell confocal imaging following published protocols (Si Y, et al. Cancer Gene Therapy. Cancer Gene Therapy. 2020; Si Y, et al. Vaccines (Basel) 2021 Aug. 10; 9(8):882; Ou J, et al. PLOS ONE. 2018; Si Y, et al. Eng Life Sci. 2021 21(1-2):37-44; Ou J, et al. J Biol Eng. 2019 13:34). Briefly, the human MDA-MB-468 cells and mouse TNBC 4T1 cells were seeded in glass bottom μ-slide with a density of $5\times10^4$ cells/mL in 100 μL medium per well. BacMam GFP Transduction Control and NucBlue Live ReadyProbes were used to stain cytoplasm and nucleus, respectively. Then the AF647-mAb was added to cells with final concentration of 1 μg of mAb/well. The live-cell images were captured at 2 hrs and 24 hrs after adding mAb using a Nikon A1R-HD25 confocal microscope with a high-speed resonance scanner (Nikon USA, Melville, NY, USA).

In Vitro Cytotoxicity Assay

The human and mouse TNBC cells were seeded in 96-well plates with density of $1\times10^5$ cells/mL for MDA-MB-468 and MDA-MB-231 and $5\times10^4$ cells/mL for 4T1. The anti-CD276 mAb-DM1 ADC was added into each well to reach the final dosages of 0, 2, 4, 10, 20, 50, 100, 200 nM. The treated cells were incubated at 37° C. and 5% $CO_2$ for three days and the cell viability was analyzed using MTT Cell Proliferation Assay kit (31, 42). The absorbance of each well, including the blank (medium), was measured at 570 nm in a microplate plate reader (BioTek, Winooski, VT, USA). The relative cell viability was calculated as: (absorbance of treated cells—absorbance of blank medium)/(absorbance of untreated cells—absorbance of blank medium)×100%.

In Vivo Imaging System (IVIS)

Both human TNBC MDA-MB-468-FLuc xenograft NSG (NOD scid gamma, Jackson Lab) mice and mouse TNBC 4T1-FLuc xenograft BALB/cJ mice were subcutaneously (s.c.) injected with $5\times10^6$ cells each mouse to generate immunocompromised models and immunocompetent models, respectively. When the tumors volume reached 50-100 $mm^3$, 40 μg of anti-CD276 mAb which was labeled with cyanine-5.5 fluorescent dye (Lumiprobe, Hunt Valley, MD, USA) was intravenously (i.v.) injected into the mouse via tail vein. The live-animal images were captured at 24 hrs post-injection with i.p. injection of FLuc substrate. Then the mice were sacrificed to harvest major organs, including brain, heart, lung, spleen, liver, and kidneys, and tumors for ex vivo imaging. The excitation/emission wavelength of 660/710 nm and exposure time of 5 seconds were used in IVIS imaging.

Cell Line-Derived Xenograft and In Vivo Treatment

The 4T1-FLuc cells ($5\times10^6$ cells per mouse) were s.c. injected to 6-week BALB/cJ female mice and tumor growth was monitored every other day. When the average tumor volume reached 50-100 $mm^3$, mice were randomized into four groups (n=7) and i.v. injected with PBS (control), 8 mg/kg of mAb (control), 8 mg/kg of ADC and 20 mg/kg of ADC following a Q4Dx4 schedule. Tumor size was measured by an electric caliper and tumor volume was calculated as $(\text{length}\times\text{width}^2)/2$. Tumor size and mice body weight were monitored twice a week. Mice were sacrificed when the tumor volume in control group reached >1,000 $mm^3$. All tumors were harvested for wet weight measurement and the main organs (brain, heart, lung, kidneys, liver, and spleen) were collected for further analysis.

Patient-Derived Xenograft (PDX) Model and In Vivo Treatment

The TNBC PDX model was generated following published procedure (Si Y, et al. Cancers (Basel). 2021 13(15)). Briefly, the donor mice carrying $CD276^+$ TNBC tumor were sacrificed when tumor reached 2,000-3,000 $mm^3$, and the harvested tumors were either passaged or fresh frozen in liquid nitrogen. To passage the patient-derived xenograft, the tumors were minced into small fragments (<1 $mm^3$), loaded into a 1-mL sterile syringe connected with a 16G needle (BD, Franklin Lakes, NJ, USA), and s.c. injected into the rear flank of 5~7-week-old NSG female mice with 40-50-μL implantation each mouse. The anti-TNBC efficacy of CD276 ADC was confirmed in PDX model by i.v. injecting PBS and 8 mg/kg ADC on a Q4Dx4 schedule (n=7).

Hematoxylin and Eosin (H & E) Staining

The slides of paraffin sectioned organs were dewaxed with xylene and hydrated with gradient ETOH (100%-50%) and $dH_2O$, followed with hematoxylin staining, dipping in 1% HCl and 70% ETOH, immersing in 1% $NH_4OH$ for blue color development, and staining with eosin for 30 secs. Finally, the stained slides were dehydrated in 95% and 100% ethanol and cleared in xylene. The H & E-stained slides were imaged with Lionheart FX Automated Microscope (BioTek, Winooski, VT, USA).

Statistical Analysis

All experimental data were presented as mean±standard error of the mean (SEM). The significance of difference among groups was analyzed using two-tailed t test and the difference between two groups was analyzed using one-way ANOVA followed by post-hoc (Dunnett's) analysis. Statistical analysis was performed using GraphPad Prism and p-value of <0.005 was used for all tests.

Results

CD276 Expression in TNBC Patient Tissues

Figure 1B:
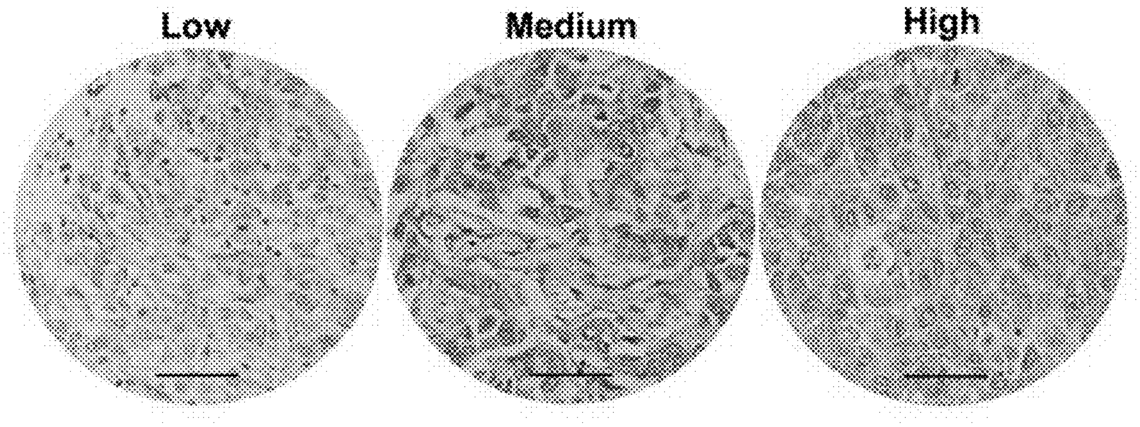

The expression of CD276 receptor was evaluated using TNBC patient tissue microarray slide with IHC staining (FIG. 1A). The receptor expression analysis with ImageJ showed that 17 of 126 TNBC tissues (14%) had high level of CD276 expression with score of >10, 58 (46%) samples had medium expression with score of 6-10, 38 (30%) samples had low expression with score of 3-6, and 13 (10%) samples had no or minimal expression with score of <3. Total of 60% TNBC tumor tissues had high or medium CD276 expression. The representative IHC staining images of TNBC patient tissues with low, medium and high levels of CD276 expression were described in FIG. 1B. These data indicated that CD276 receptor is a potential target to develop anti-TNBC therapies.

Anti-CD276 mAb Development and Production

Figure 2A:
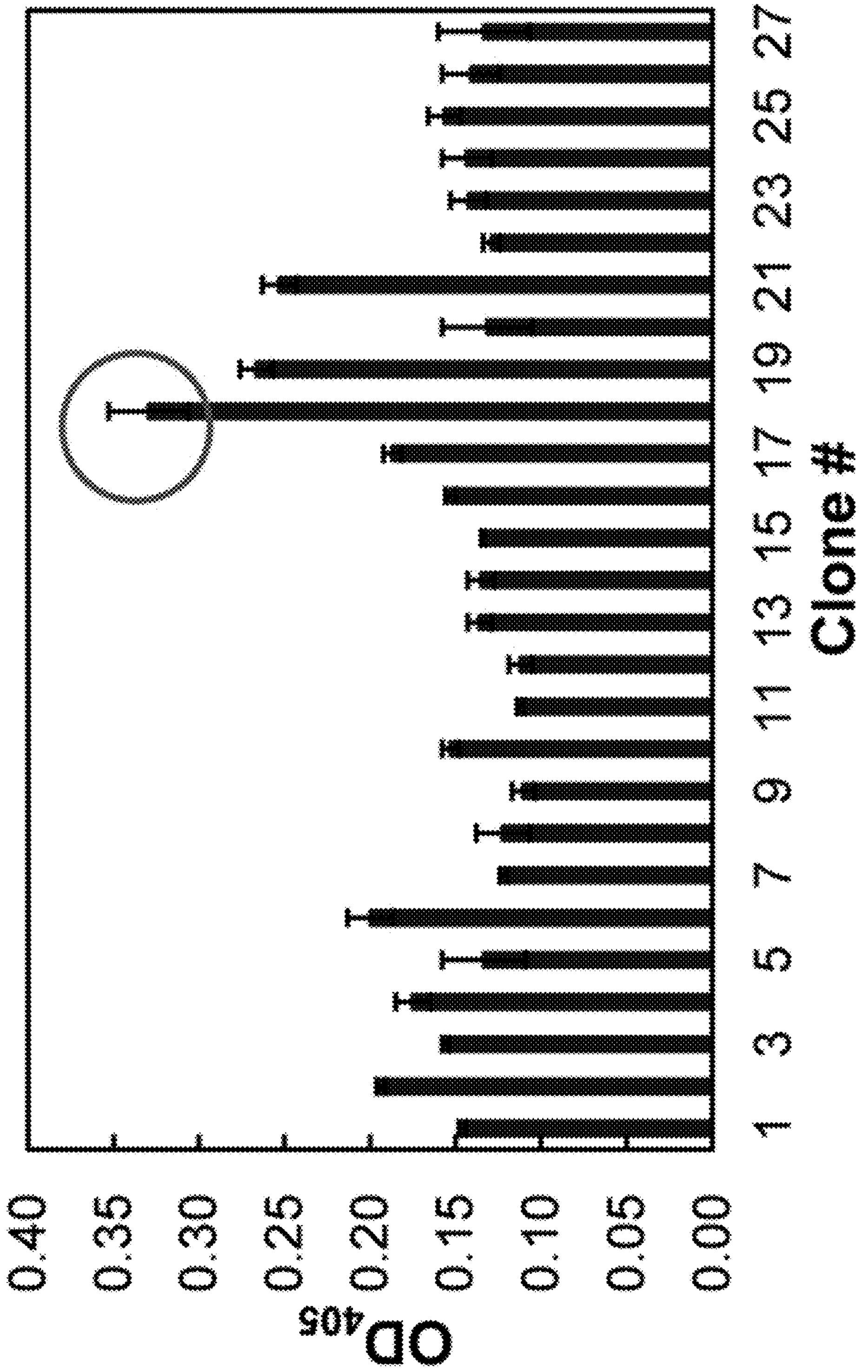
FIG. 2A shows IHC staining of TMA with anti-CD276 antibody.
Figure 2B:
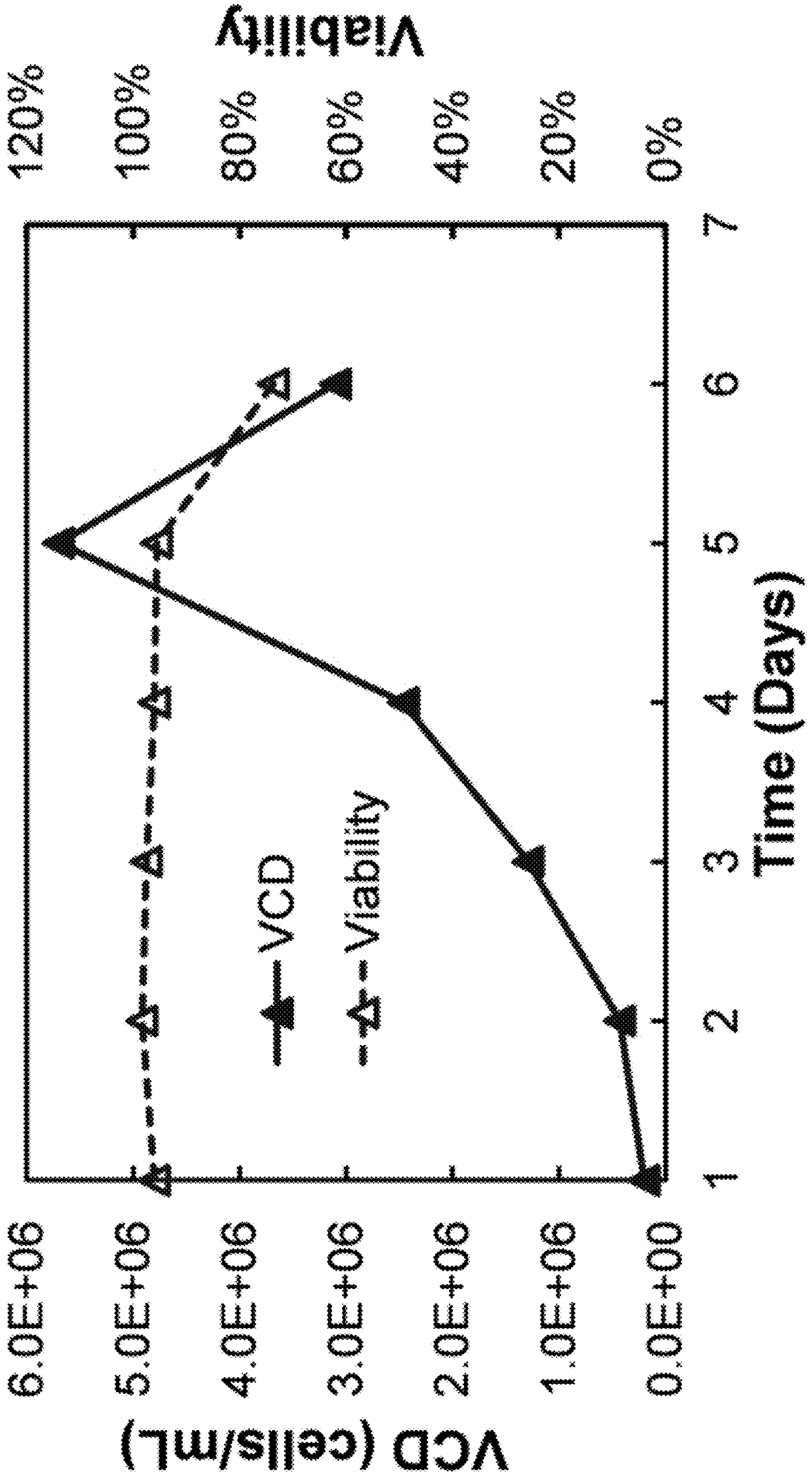
Figure 2C:
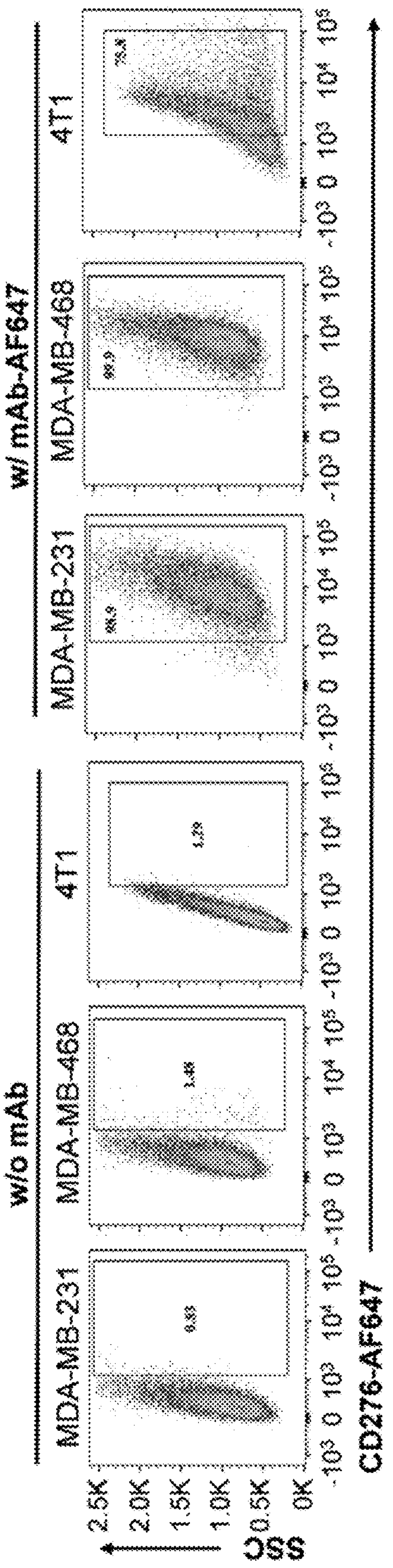

The top CD276 mAb-producing hybridoma clone was screened using enzyme-linked immunosorbent assay (ELISA) with HEK293 expressed glycosylated extracellular peptide (Leu29-Pro245) as the coating antigen (FIG. 2A). The top clone with the highest CD276 mAb production was screened and further adapted to suspension culture in serum-free media (SFM). The fed-batch production culture fed with glucose, glutamine and cell boost #6 reached peak viable cell density (VCD) of $5.7\times10^6$ cells/mL (FIG. 2B) and final mAb titer of 45-50 mg/L. The isotype analysis revealed that the developed CD276 mAb was IgG2b/kappa. The TNBC surface binding rates of CD276 mAb were analyzed in cell lines MDA-MB-231, MDA-MB-468 and 4T1 using flow cytometry analysis (FIG. 2C). The CD276 mAb-AF647 showed high surface binding rates of 98.9% and 99.9% to human TNBC MDA-MB-231 and MDA-MB-468 cells, respectively, and 75.8% to mouse TNBC 4T1 cells under the same staining conditions. The human CD276 (UniProtKB Q5ZPR3) and mouse CD276 (UniProtKB Q8VE98) have the same topology including one extracellular, one helical transmembrane, and one cytoplasmic domain. Protein BLAST analysis showed that the human and mouse CD276 receptors have similarity of 93%. These data suggested that the anti-CD276 mAb can target both human and mouse TNBC cells with a high binding rate. The human TNBC xenograft mouse model is feasible to be used to evaluate the tumor targeting of the developed mAb and ADC in vivo.

In Vitro and In Vivo TNBC-Targeting

Figure 3:
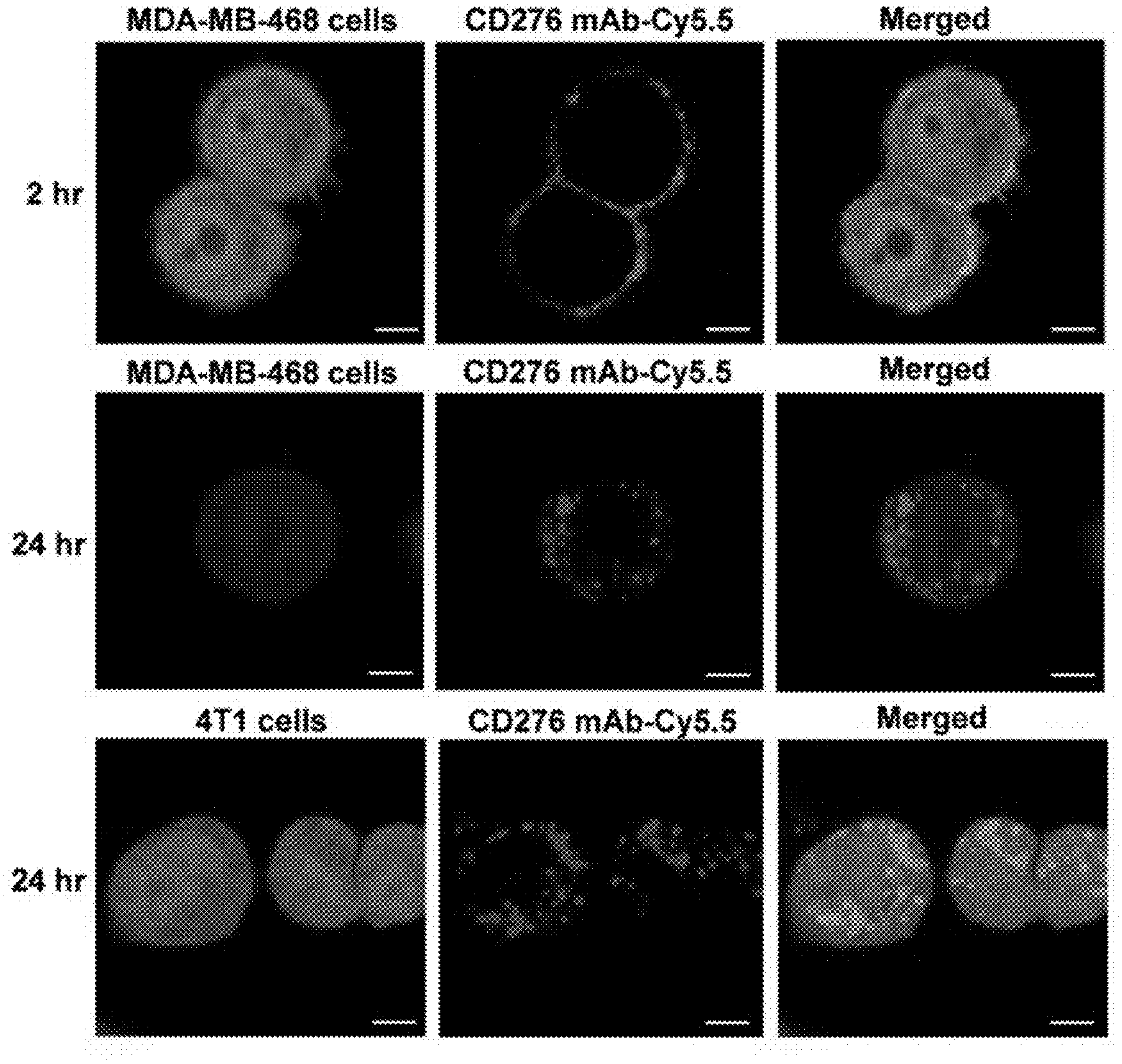
FIG. 3: TNBC targeting and internalization of anti-CD276 mAb. Obvious surface binding of CD276 mAb was observed at 2 hrs after mixing the AF647 fluorescent dye labelled anti-human/mouse CD276 mAb (red) with human TNBC cells (MDA-MB-468) and mouse TNBC cells (4T1) (green), and mAb effectively internalized into TNBC cells at 24 hrs.

To visualize the surface binding and receptor mediated internalization, the anti-CD276 mAb was labelled with fluorescent dye AF647. The live-cell confocal microscopy imaging demonstrated that AF647-mAb bound the TNBC MDA-MB-468 and 4T1 cells (BacMam GFP expressed in cytoplasm) at 2 hrs after mixing mAb and cells (FIG. 3). The CD276 mAb-AF647 effectively internalized into TNBC cells via receptor-mediated endocytosis within 24 hrs after forming complex. These images demonstrated that the anti-CD276 mAb can target TNBC cells and release payload intracellularly.

Figure 4A:
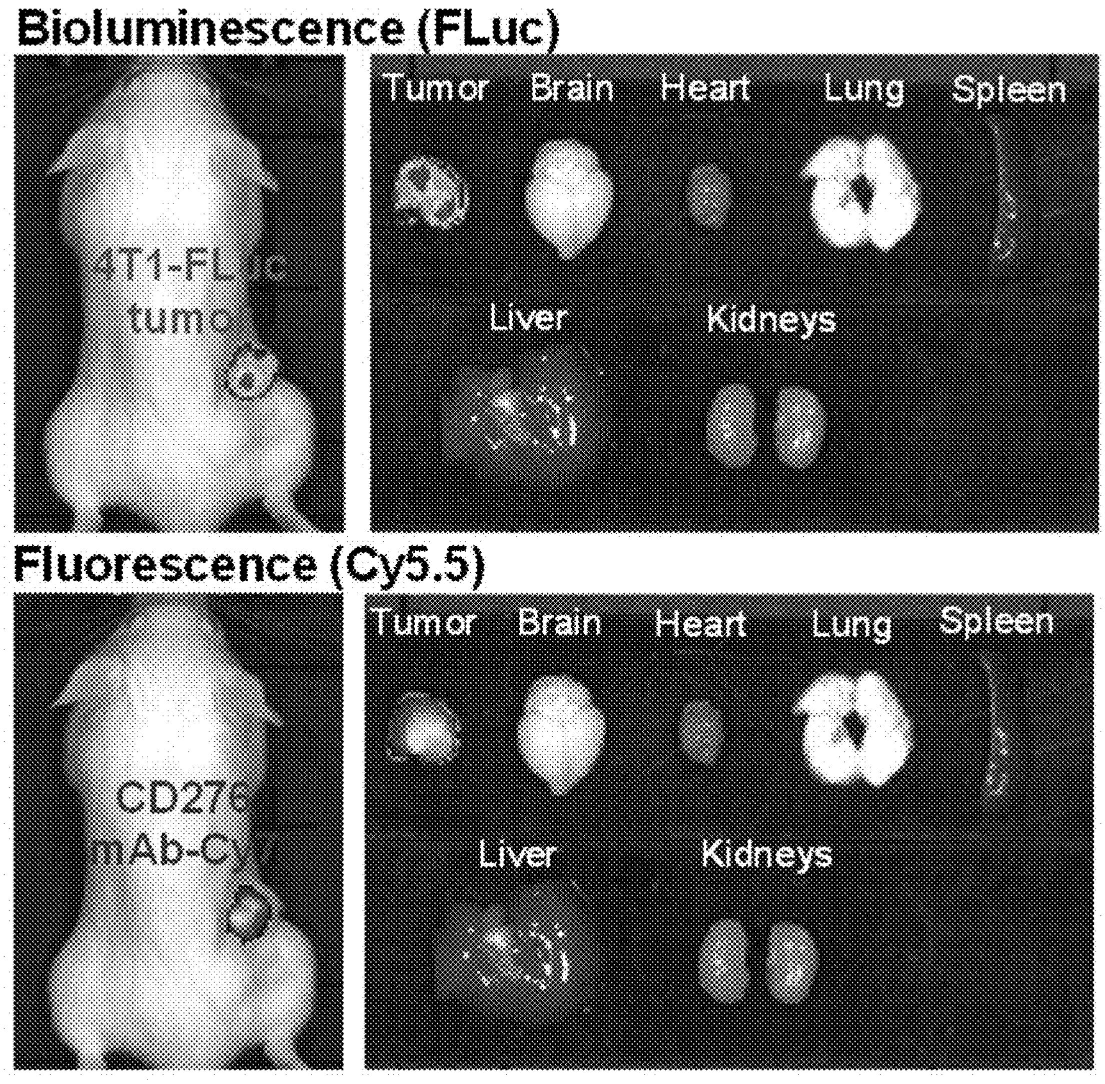
FIGS. 4A and 4B: In vivo evaluation of TNBC targeting by anti-CD276 mAb.
Figure 4B:
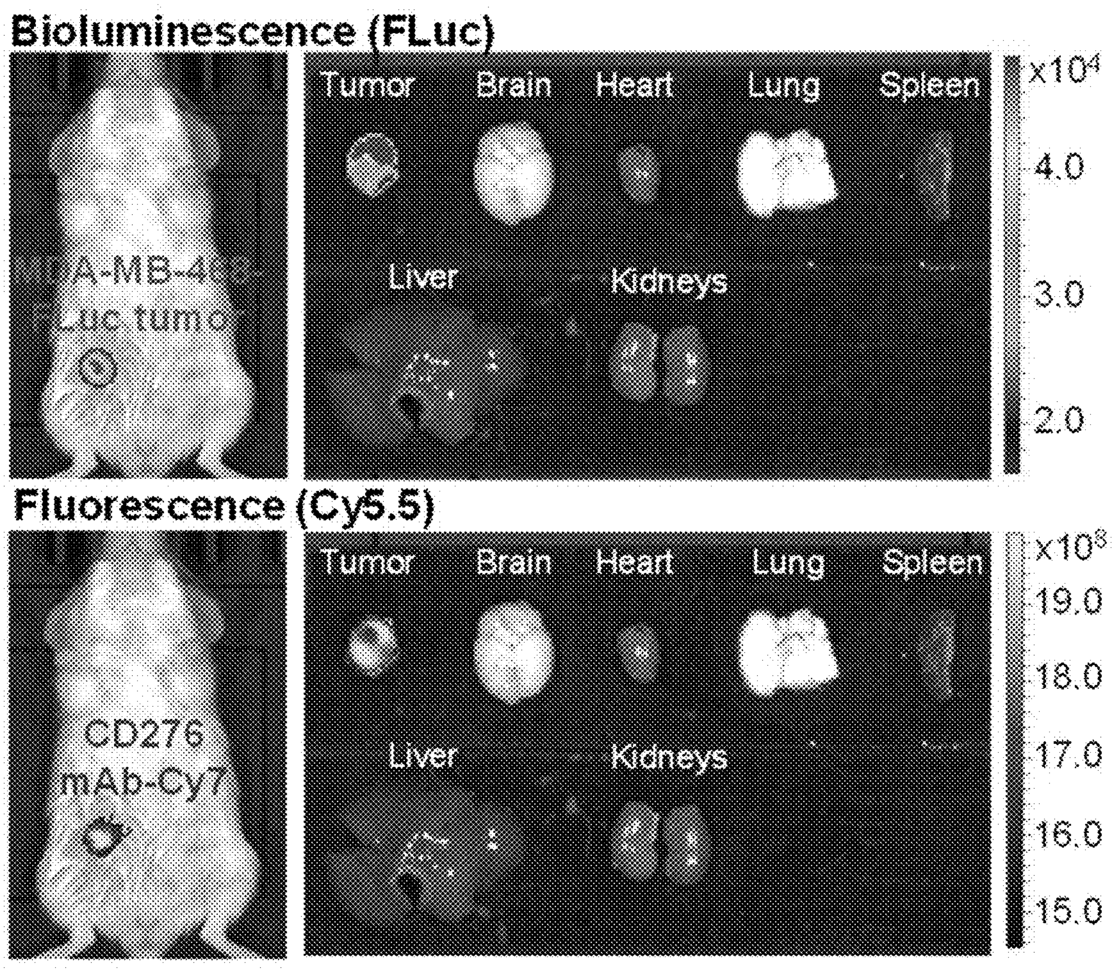

The MDA-MB-468-FLuc and 4T1-FLuc xenografted mouse models were used to further evaluate the TNBC-targeting and biodistribution of CD276 mAb-Cy5.5 using live-animal and ex vivo IVIS imaging. As shown in FIG. 4, the bioluminescent signal (FLuc, tumor) was co-localized with the fluorescent signal (Cy5.5, mAb), which suggested the in vivo TNBC-targeting of the mAb. The ex vivo images showed strong fluorescent signal in tumors while no or un-detectable signal in the major organs such as brain, heart, lung, spleen, liver, and kidneys. These IVIS images indicated that the anti-CD276 mAb was able to specifically bind and accumulate in both human and mouse TNBC tumors and also suggested its capability to targeting deliver payload for TNBC treatment.

ADC Construction and In Vitro Anti-TNBC Cytotoxicity

Figure 5A:
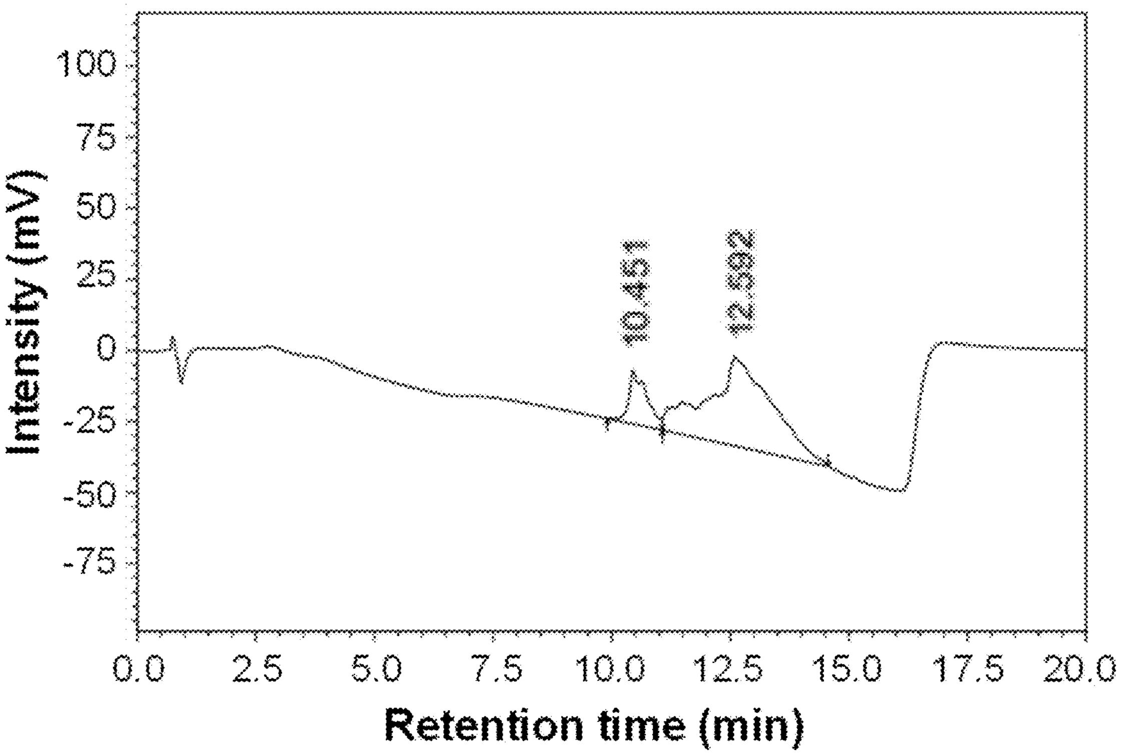
FIGS. 5A to 5B. DAR and in vitro cytotoxicity.

The purity, conjugation rate and DAR of CD276 ADC were analyzed using an HPLC procedure. These results showed that the antibody-drug conjugation rate was >90%, the ADC purity was >95%, and the calculated DAR was >4 (FIG. 5A). It is clear that the anti-CD276 mAb-DM1 conjugate was successfully constructed with high yield, conjugation efficiency and integrity.

Figure 5B:
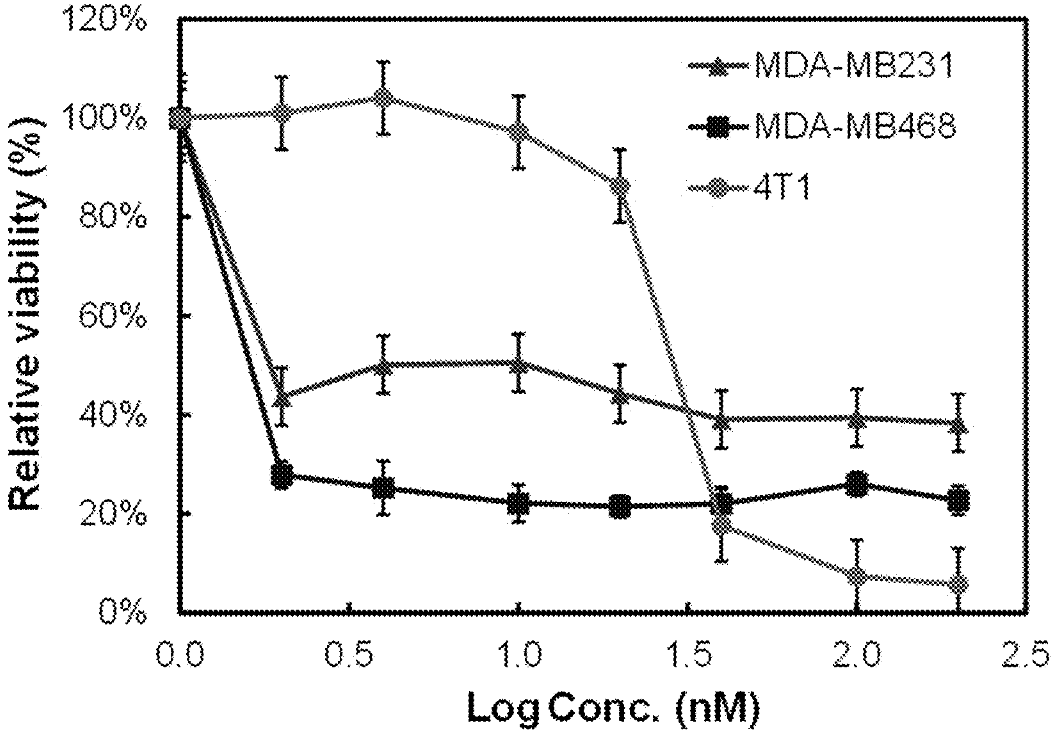

The in vitro anti-cancer cytotoxicity of the constructed anti-CD276 mAb-DM1 (ADC) was tested in a three-day $IC_{50}$ assay using three TNBC cell lines, such as MDA-MB-231, MDA-MB-468 and 4T1 cells. A serial dosages of 0, 2, 4, 10, 20, 50, 100, and 200 nM were tested, which reduced cell viability to 100%, 44%, 50%, 51%, 44%, 39%, 39%, and 38% for MDA-MB-231 cells, 100%, 28%, 25%, 22%, 21%, 22%, 26%, and 23% for MDA-MB-468 cells, and 100%, 101%, 104%, 97%, 86%, 18%, 7%, and 6% for 4T1 cells, respectively (FIG. 5B). The $IC_{50}$ of ADC was 1.6 nM, 1.4 nM and 26 nM for MDA-MB-231, MDA-MB-468 and 4T1 cells, respectively. These in vitro cytotoxicity data shows that the anti-CD276 ADC had high potency to treat TNBC cells.

In Vivo Anti-Tumor Efficacy in 4T1 Xenograft Models

Figure 6A:
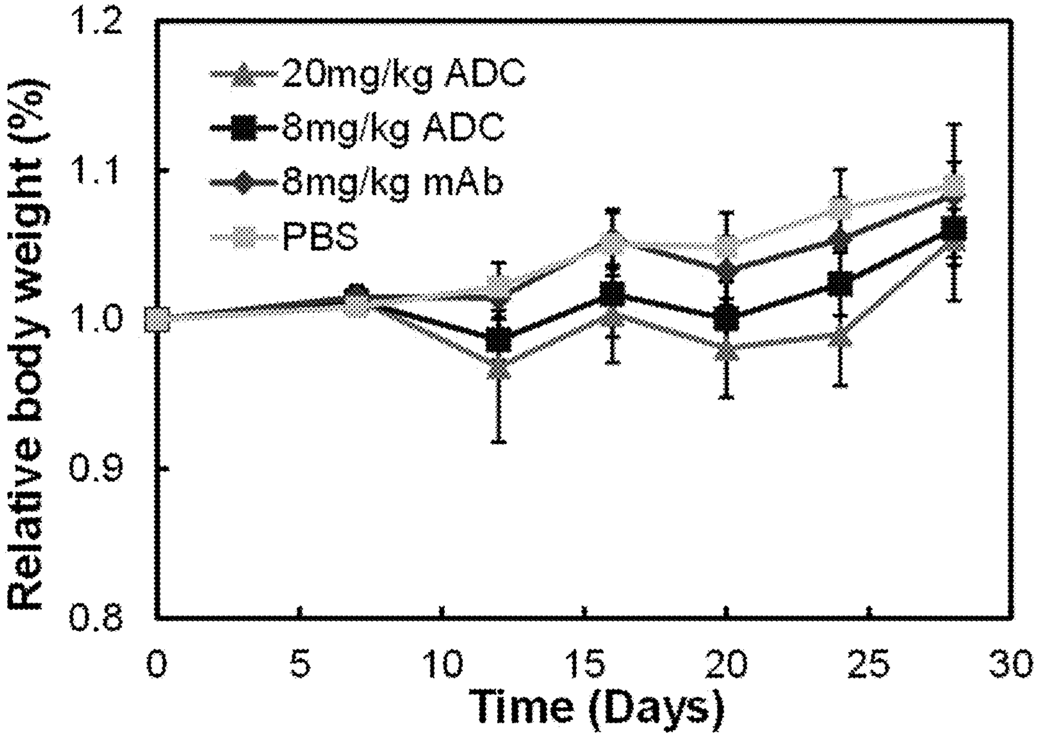
FIGS. 6A to 6C. In vivo anti-TNBC efficacy of anti-CD276 ADC in 4T1-FLuc xenograft mouse models.
Figure 6B:
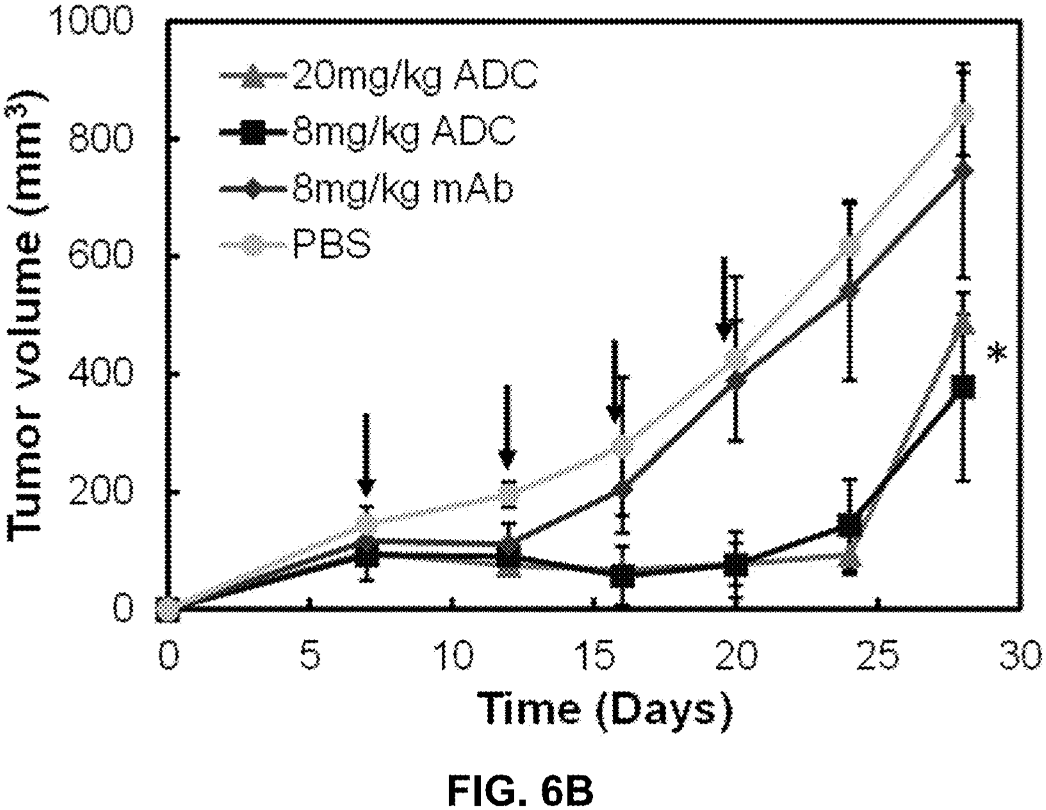
Figure 6C:
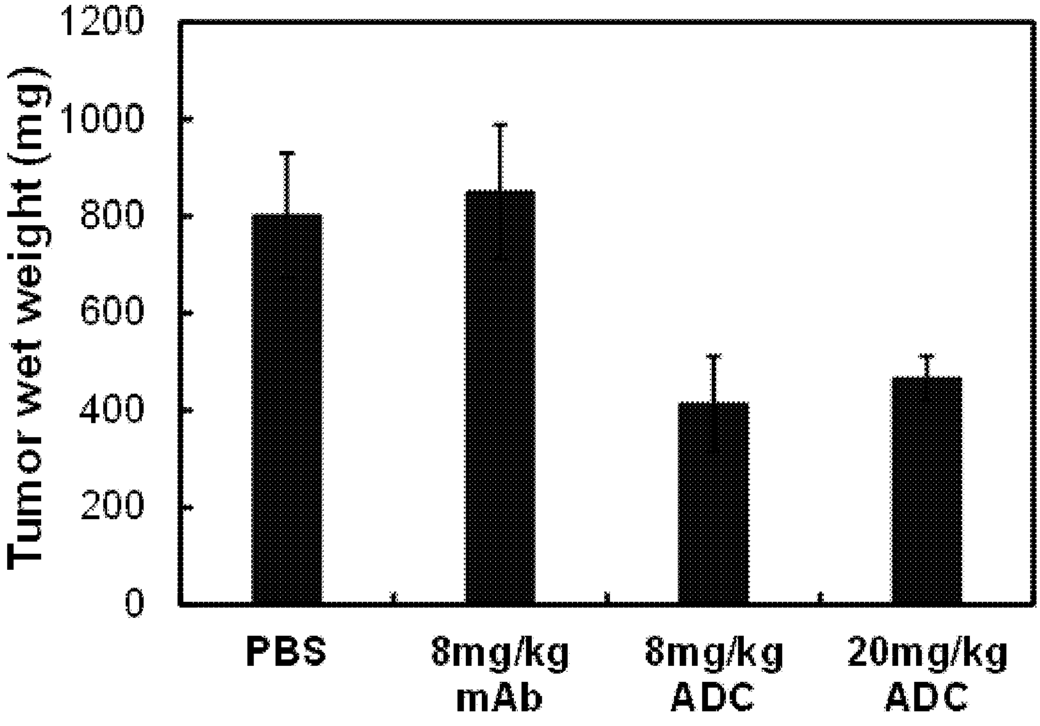

The in vivo anti-tumor efficacy of CD276 ADC was first evaluated in 4T1-FLuc xenograft models. When tumor volume reached 50-100 $mm^3$, the mice were i.v. administrated with PBS (control), 8 mg/kg of mAb, 8 mg/kg of ADC, and 20 mg/kg of ADC following a Q4Dx4 schedule. As shown in FIG. 6A, the change of body weight was <10% during the treatment period and there was no obvious difference among groups. As compared to the PBS or mAb control groups, the treatment with 20 mg/kg of ADC or 8 mg/kg of ADC inhibited tumor growth during treatment and reduced tumor growth in the end of this study (FIGS. 6B and 6C). The recurrence at 8 days post treatment could be caused by the relatively lower mouse TNBC-binding rate of anti-CD276 mAb. This study demonstrated the promising anti-tumor efficacy of the CD276 ADC.

In Vivo Anti-TNBC Efficacy in PDX Models

Figure 7A:
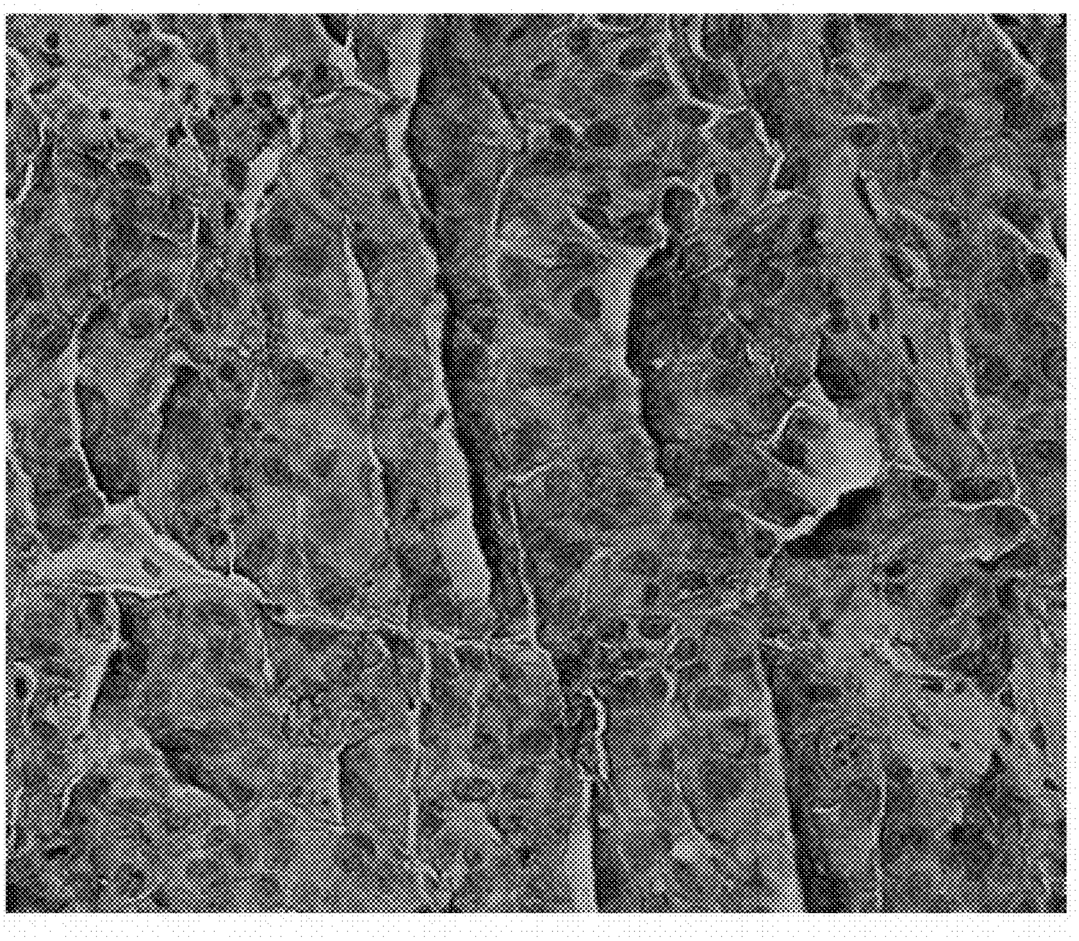
FIGS. 7A to 7D. In vivo anti-tumor efficacy of anti-CD276 ADC in TNBC PDX models.
Figure 7B:
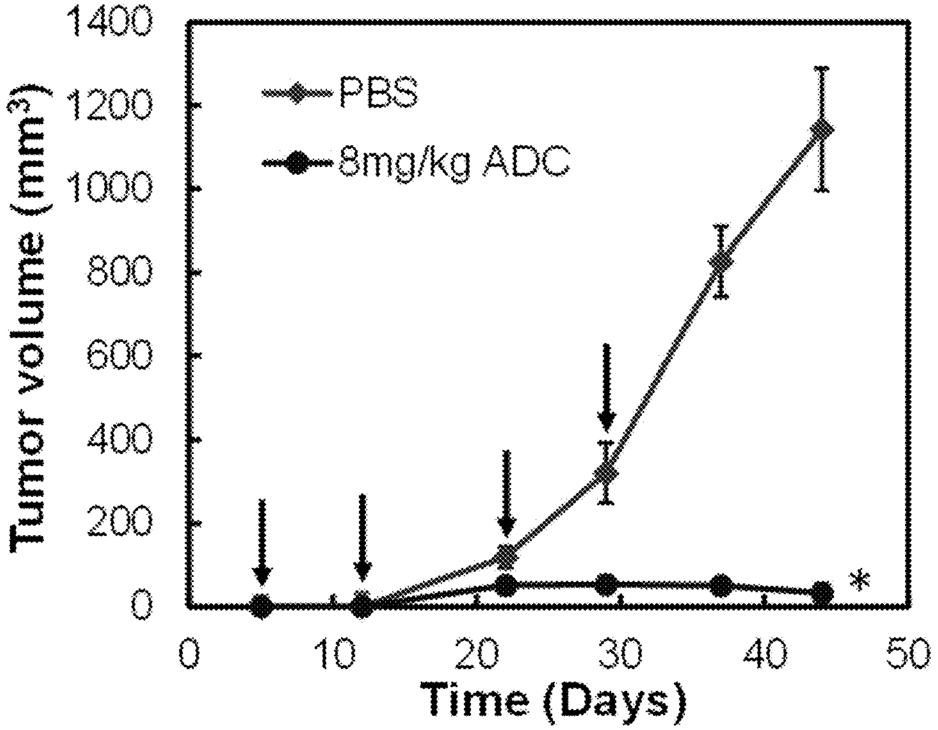
Figure 7C:
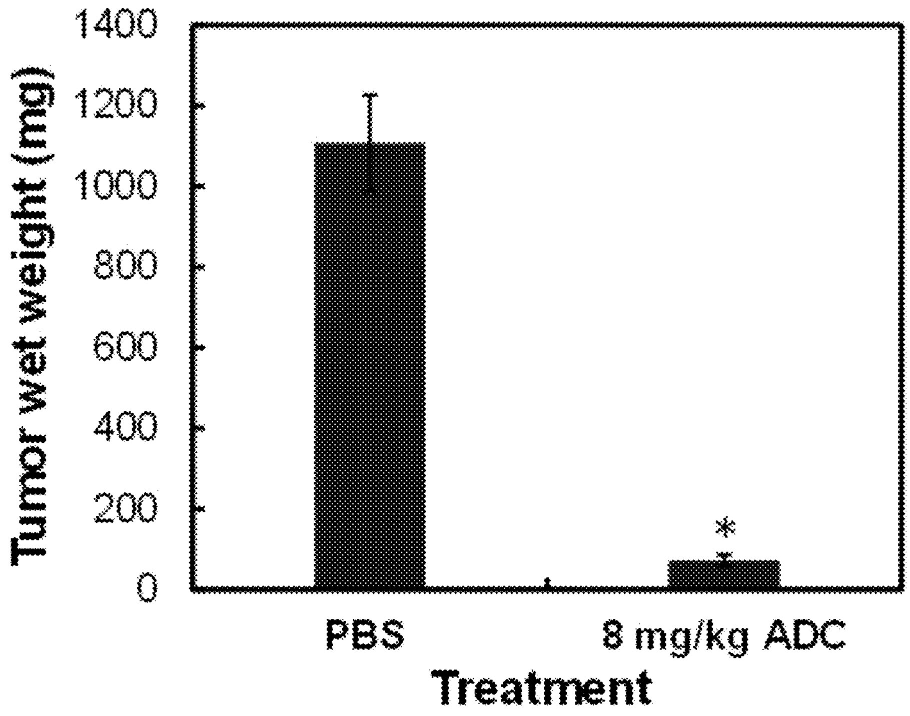
Figure 7D:
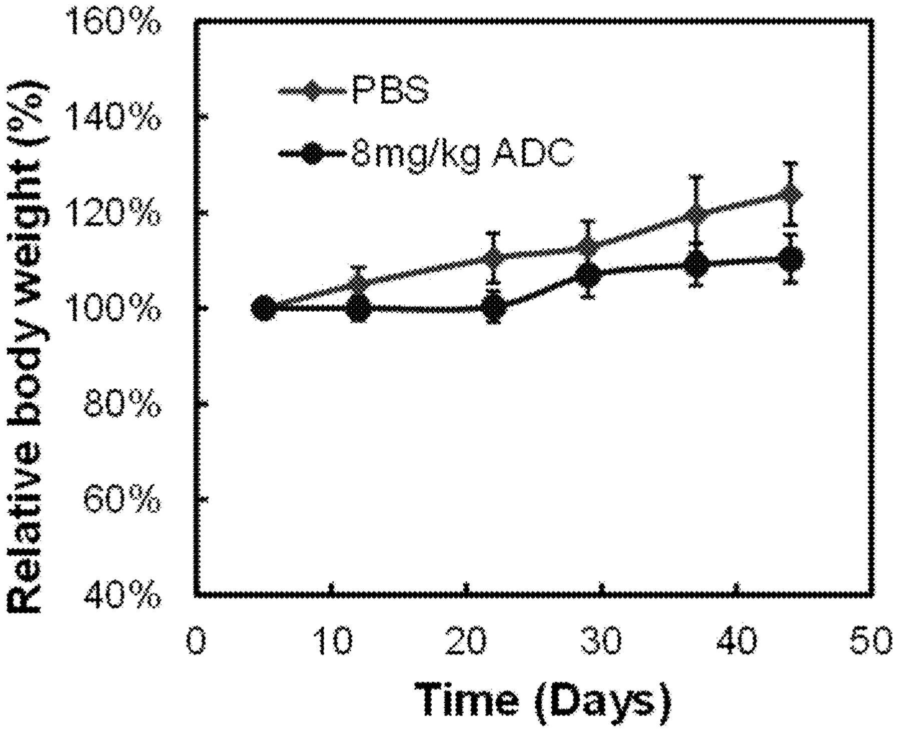

To better evaluate or confirm the anti-TNBC efficacy of CD276 ADC, a $CD276^+$ PDX model was established. The CD276 expression was confirmed with the PDX tumor tissue section slide (FIG. 7A). Treated with PBS (negative control) and 8 mg/kg of ADC, the PDX xenograft tumor growth was completely inhibited and there was no tumor recurrence observed after stopping treatment (FIG. 7B). The wet weight of harvested tumors confirmed the measured tumor volume data (FIG. 7C). All these data showed that the anti-CD276 ADC could effectively treat TNBC.

Toxicity Analysis with H & E Staining and Whole Blood Analysis

Figure 8:
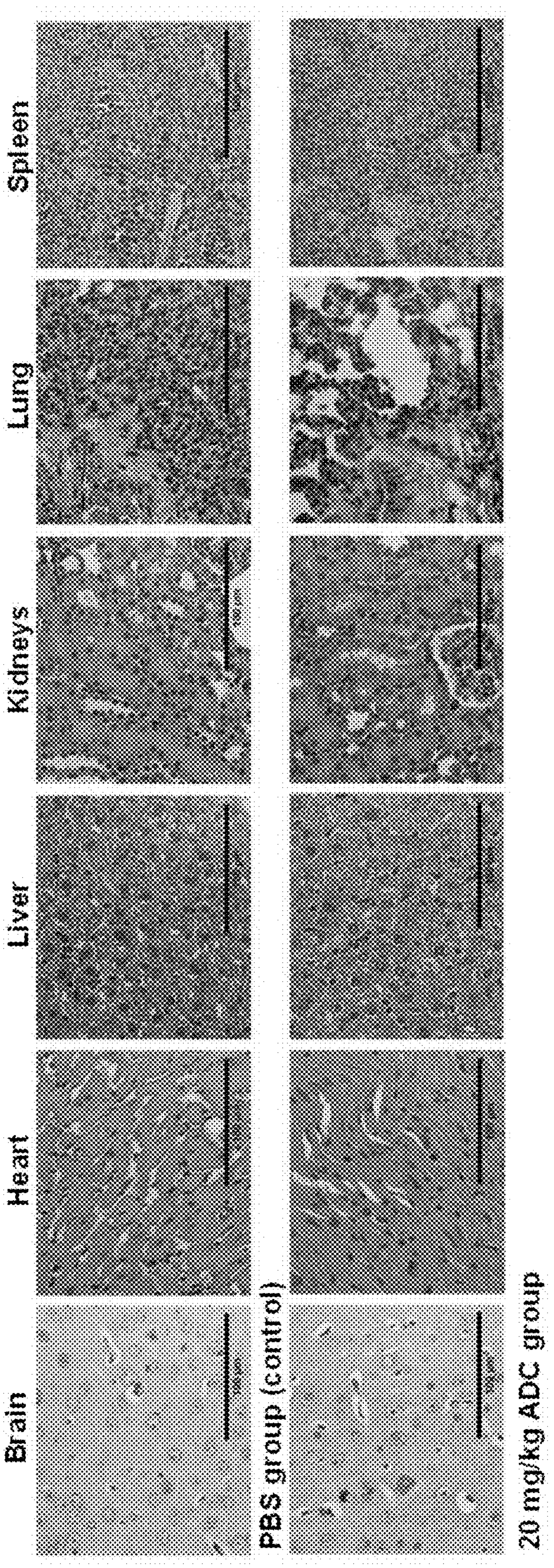
FIG. 8. Evaluation of the possible toxicity of anti-CD276 ADC or mAb in BALB/cJ mice. H & E staining of major organs (brain, heart, liver, kidney, lung, and spleen) at 28 days post i.v. injection of 20 mg/kg ADC via tail vein. Scale bar equals to 100 μm. n=7.

The main organs, including brain, heart, liver, kidneys, lung, and spleen, harvested from the in vivo study in 4T1-FLuc xenografted BALB/cJ mouse models were sectioned and performed with H & E staining. There was no obvious difference of cell morphology between ADC treatment group and PBS control group (FIG. 8A). The further whole blood analysis showed that leukocytes were in normal range of 1.8~10.7K/μL for white blood cells, 0.1~2.4K/μL for neutrophil, and 0.9~9.3K/μL for lymphocytes (FIG. 8B). No significant difference of red blood cells (M/μL), hemoglobin (g/dL) and platelets (K/μL) was observed between the control and mAb groups. There was no anemia or blood clot observed within two weeks post-mAb injection. All these data indicated the safety and minimal toxicity of anti-CD276 ADC for TNBC treatment.

Discussion

In this study, the expression of CD276 receptor as evaluated and confirmed in around 60% of TNBC patient tissues. This finding was consistent with previous studies that detected CD276 in more than 80% of breast cancer tissues (Sun J, et al. Onco Targets Ther. 2014 7:1979-86; Bachawal S V, et al. Cancer Res. 2015 75(12):2501-9; Liu C, et al. Mol Med Rep. 2013 7(1):134-8). The recent clinical trials of enoblituzumab for prostate, breast and lung cancers treatment (Picarda E, et al. Clin Cancer Res. 2016 22(14):3425-31) demonstrated the minimal toxicity to target CD276. In addition, CD276 is involved in inhibiting the immune functions of natural killer (NK) and T cells and the production of effector cytokines (Pardoll D M. Nat Rev Cancer. 2012 12(4):252-64; Vigdorovich V, et al. Structure. 2013 21(5): 707-17; Chen C, et al. Exp Cell Res. 2013 319(1):96-102), so blocking the CD276 signaling pathway could reactivate the immune functions of NK and T cells in tumor microenvironment (Picarda E, et al. Clin Cancer Res. 2016 22(14): 3425-31; Maeda N, et al. Ann Surg Oncol. 2014 21 Suppl 4:S546-54). Targeting CD276 is a good strategy to treat TNBC because it could cover the majority of TNBC patients and might also upregulate the immunity in tumor microenvironment. A new anti-CD276 mAb and ADC was developed and their anti-TNBC effects evaluated both in vitro and in vivo.

The Fc-fused fragment cloned from the extracellular domain of human CD276 was expressed in HEK293 cells to generate the same glycan structure as human antigen. This N-glycosylated peptide was injected as immunogen to generate anti-human CD276 mAb using hybridoma technology, which is expected to have high CD276 specificity. As presented in this study, the top anti-CD276 mAb clone (IgG2b/kappa) showed high TNBC-targeting and drug delivery capability in flow cytometry analysis and IVIS imaging, which was further confirmed by the anti-TNBC cytotoxicity and anti-tumor efficacy studies. In addition to the direct cancer cell death caused by the microtubulin depolymerization via potent DM1 in ADC, which was investigated in this study, the synergism of the upregulation of immune function in tumor microenvironment by anti-CD276 mAb could significantly improve the anti-TNBC therapeutic effects.

To fully evaluate the anti-TNBC efficacy, a $CD276^+$ PDX model was successfully identified, established, passaged and maintained. The in vivo evaluation of the new anti-CD276 ADC in PDX models confirmed its TNBC treatment effects, as indicated by the completely inhibited tumor growth post i.v. injection. The PDX models could recapitulate the biological nature, genetic and histological features and biological behaviors correlating with the high metastasis, high heterogeneity and poor survival of primary TNBC tumors. This model can be used to evaluate the therapeutic efficacy of different targeted therapies in future.

CONCLUSIONS

In this study, a new anti-CD276 mAb was developed to target $CD276^+$ TNBC and deliver potent payload to achieve high anti-cancer cytotoxicity and reduce side effects. Moreover, the CD276 mAb has great potential to reactivate the immune functions of NK and T cells in tumor microenvironment, which needs a full evaluation in future study. The anti-CD276 mAb-based ADC could provide an effective targeted therapy with integrated anti-TNBC mechanisms, which needs further investigation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-human CD276 antibody that selectively binds the extracellular domain of CD276 (Leu29-Pro245), comprising a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence GYTFTEYT (SEQ ID NO:1);

the CDR2 sequence of the $V_H$ domain comprises the amino acid sequence NNPNTGGT (SEQ ID NO:2);

the CDR3 sequence of the $V_H$ domain comprises the amino acid sequence SRSGNDVGWYFAV (SEQ ID NO:3);

the CDR1 sequence of the $V_L$ comprises the amino acid sequence SSVSY (SEQ ID NO:4);

the CDR2 sequence of the $V_L$ domain comprises the amino acid sequence DTS; and the CDR3 sequence of the $V_L$ domain comprises the amino acid sequence QQWSSNPLT (SEQ ID NO:5).

2. The antibody of claim 1, wherein the $V_H$ domain comprises the amino acid sequence SEQ ID NO:6.

3. The antibody of claim 1, wherein the $V_L$ domain comprises the amino acid sequence SEQ ID NO:7.

4. The antibody of claim 1, wherein the antibody is a monoclonal antibody.

5. The antibody of claim 1, wherein the antibody is a recombinant antibody.

6. The antibody of claim 5, wherein the recombinant antibody is a single chain antibody (scFv).

7. The antibody of claim 6, wherein the $V_H$ domain comprises the amino acid sequence SEQ ID NO:9 and wherein the $V_L$ domain comprises the amino acid sequence SEQ ID NO:10.

8. An antibody drug conjugate (ADC) comprising a chemotherapeutic agent conjugated to the antibody of claim 1.

9. The ADC of claim 8, wherein the chemotherapeutic agent comprises cetuximab.

10. A method of treating breast cancer in a subject, comprising administering an effective amount of the ADC of claim 8, in a pharmaceutically acceptable carrier.

11. The method of claim 10, further comprising administering to the subject an ADC comprising a chemotherapeutic agent conjugated to an anti-EGFR antibody.

12. The method of claim 11, wherein the breast cancer is triple-negative breast cancer.

* * * * *

SEQUENCE LISTING

```
Sequence total quantity: 10
SEQ ID NO: 1            moltype = AA  length = 8
FEATURE                 Location/Qualifiers
source                  1..8
                        mol_type = protein
                        organism = unidentified
SEQUENCE: 1
GYTFTEYT                                                     8

SEQ ID NO: 2            moltype = AA  length = 8
FEATURE                 Location/Qualifiers
source                  1..8
                        mol_type = protein
                        organism = unidentified
```

```
SEQUENCE: 2
NNPNTGGT                                                               8

SEQ ID NO: 3            moltype = AA  length = 13
FEATURE                 Location/Qualifiers
source                  1..13
                        mol_type = protein
                        organism = unidentified
SEQUENCE: 3
SRSGNDVGWY FAV                                                         13

SEQ ID NO: 4            moltype = AA  length = 5
FEATURE                 Location/Qualifiers
source                  1..5
                        mol_type = protein
                        organism = unidentified
SEQUENCE: 4
SSVSY                                                                  5

SEQ ID NO: 5            moltype = AA  length = 9
FEATURE                 Location/Qualifiers
source                  1..9
                        mol_type = protein
                        organism = unidentified
SEQUENCE: 5
QQWSSNPLT                                                              9

SEQ ID NO: 6            moltype = AA  length = 120
FEATURE                 Location/Qualifiers
source                  1..120
                        mol_type = protein
                        organism = unidentified
SEQUENCE: 6
EVQLQQSGPE LVKPGASVKI SCKTSGYTFT EYTMHWVKQS HGKSLEWIGS NNPNTGGTTY  60
NQKFKDKATL TVDKSSNTAY MELRSLTSDD SAVYYCSRSG NDVGWYFAVW GAGTTVTVSS  120

SEQ ID NO: 7            moltype = AA  length = 107
FEATURE                 Location/Qualifiers
source                  1..107
                        mol_type = protein
                        organism = unidentified
SEQUENCE: 7
QIVLTQSPAI MSASPGEKVT MTCTATSSVS YMHWYQQKSD SSPKRWIYDT SKLASGVPDR  60
FSGSGSGTSY SLIISSMEAE DAATYYCQQW SSNPLTFGAG TKLELKR                107

SEQ ID NO: 8            moltype = AA  length = 15
FEATURE                 Location/Qualifiers
source                  1..15
                        mol_type = protein
                        organism = unidentified
SEQUENCE: 8
GGGGSGGGGS GGGGS                                                       15

SEQ ID NO: 9            moltype = AA  length = 469
FEATURE                 Location/Qualifiers
source                  1..469
                        mol_type = protein
                        organism = unidentified
SEQUENCE: 9
MGWSWIFLFL LSGTAGVLSE VQLQQSGPEL VKPGASVKIS CKTSGYTFTE YTMHWVKQSH  60
GKSLEWIGSN NPNTGGTTYN QKFKDKATLT VDKSSNTAYM ELRSLTSDDS AVYYCSRSGN  120
DVGWYFAVWG AGTTVTVSSA KTTAPSVYPL APVCGDTTGS SVTLGCLVKG YFPEPVTLTW  180
NSGSLSSGVH TFPAVLQSDL YTLSSSVTVT SSTWPSQSIT CNVAHPASST KVDKKIEPRG  240
PTIKPCPPCK CPAPNLLGGP SVFIFPPKIK DVLMISLSPI VTCVVVDVSE DDPDVQISWF  300
VNNVEVHTAQ TQTHREDYNS TIRVVSTLPI QHQDWMSGKE FKCKVNNKDL PSPIERTISK  360
IKGLVRAPQV YILPPPAEQL SRKDVSLTCL VVGFNPGDIS VEWTSNGHTE ENYKDTAPVL  420
DSDGSYFIYS KLNMKTSKWE KTDSFSCNVR HEGLKNYYLK KTISRTPGK              469

SEQ ID NO: 10           moltype = AA  length = 235
FEATURE                 Location/Qualifiers
source                  1..235
                        mol_type = protein
                        organism = unidentified
SEQUENCE: 10
MDYQVQIFSF LLISASVIIS RGQIVLTQSP AIMSASPGEK VTMTCTATSS VSYMHWYQQK  60
SDSSPKRWIY DTSKLASGVP DRFSGSGSGT SYSLIISSME AEDAATYYCQ QWSSNPLTFG  120
AGTKLELKRA DAAPTVSIFP PSSEQLTSGG ASVVCFLNNF YPKDINVKWK IDGSERQNGV  180
LNSWTDQDSK DSTYSMSSTL TLTKDEYERH NSYTCEATHK TSTSPIVKSF NRNEC        235
```